May 30, 1961 E. S. BOERNER Plant Pat. 2,058
ROSE PLANT
Filed Sept. 6, 1960
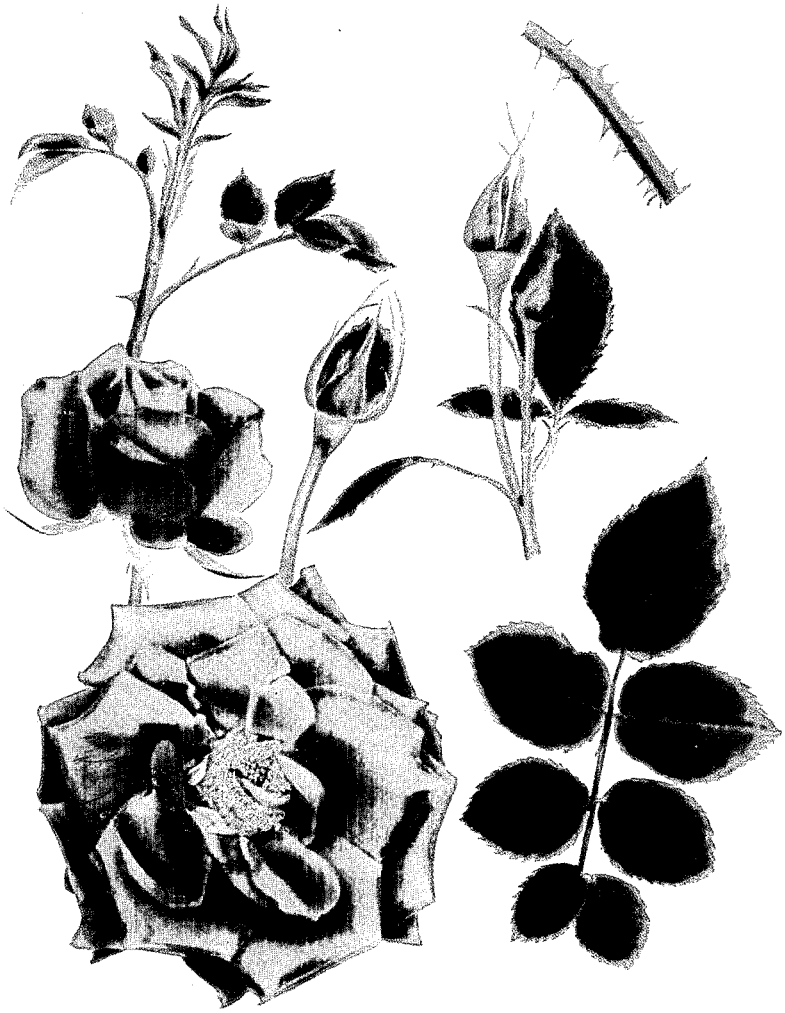
Inventor.
E. S. Boerner
By: Robb & Robb
Attorneys.

United States Patent Office

Plant Pat. 2,058
Patented May 30, 1961

2,058

ROSE PLANT

Eugene S. Boerner, Newark, N.Y., assignor to Jackson & Perkins Company, Newark, N.Y., a corporation of New York Filed Sept. 6, 1960, Ser. No. 54,332

1 Claim. (Cl. 47—61)

The present invention relates to a new and distinct variety of rose plant of the hybrid tea class, which was originated by me by crossing an unnamed and unpatented seedling of the variety named "Poinsettia" (unpatented) with the variety "New Yorker" (Plant Patent No. 823).

The primary objective of this breeding was to produce a new hybrid tea rose variety comparable to that of the parent "New Yorker," which is presently one of the most popular red rose varieties, but characterized by a larger plant and flower size. In addition, it was the further objective to achieve greater floriferousness in such a new variety as mentioned above. These objectives were fully attained, along with other desirable improvements, as evidenced by the following unique combination of characteristics which are outstanding in the new variety and which distinguish it from its parents, as well as from all other varieties of which I am aware:

(1) Abundant foliage;

(2) Tall growth (ranges from 2½–3 feet, which is taller than "New Yorker");

(3) Large flower size (averages 5½ inches); and (4) A very deep red general color tonality of the flowers, corresponding to Carmine.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed seedling of "Poinsettia."

*Pollen parent.*—"New Yorker."

Classification:

*Botanic.*—Hybrid tea.

*Commercial.*—Hybrid tea.

*Flower*

(Observations made from specimens grown outdoors at Newark, New York, in the early morning during the early part of September.)

Blooming habit: Recurrent—continuous.

Bud:

*Size.*—Large.

*Form.*—Ovoid; is not affected by wet or hot weather.

*Color.*—When sepals first divide—Oxblood Red, Plate 1. When petals begin to unfurl—Oxblood Red, Plate 1, lightly overcast with Carmine, Plate 1, at the base of petal. When half-blown: inside of petals—Carmine, Plate 1, lightly overcast with Spectrum Red, Plate 1; reverse of petals—Carmine, Plate 1, lightly overcast with Oxblood Red, Plate 1.

*Sepals.*—Serrated and slightly branched; curl back when petals begin to unfurl. Colors: inside—Absinthe Green, Plate 31; outside—Bice Green, Plate 17.

*Calyx.*—Color—light Bice Green, Plate 17. Shape—funnel. Size—large. Aspect—smooth. Odor when rubbed—none.

*Peduncle.*—Length—short. Aspect—rough. Strength—erect; slender. Color—light Bice Green, Plate 17. Opening—opens up well; is not affected by adverse weather conditions.

Bloom:

*Size.*—Large. Average size when fully opened—5½ inches.

*Borne.*—Both singly and several together.

*Stem.*—Medium length; strong.

*Form (when first open).*—High-centered. Permanence—retains its form to the end, but outer petals curl back.

*Petalage.*—Double (full but open center). Number of petals under normal conditions—from 25–30.

*Color.*—Center of flower—Carmine, Plate 1, lightly overcast with Spectrum Red, Plate 1, on the outer edge of the petal. Outer petals—Carmine, Plate 1. Base of petals (aiglet)—Martius Yellow, Plate 4. Inside of petals—Carmine, Plate 1, lightly overcast with Spectrum Red, Plate 1. Reverse of petals—Spectrum Red, Plate 1, lightly overcast with Carmine, Plate 1. General tonality from a distance—Carmine, Plate 1, with outer edge of petal very lightly overcast with Spectrum Red, Plate 1.

*Discoloration.*—General tonality at end of first day—Carmine, Plate 1. Second day—Carmine, Plate 1, lightly overcast with Spectrum Red, Plate 1. Third day—Carmine, Plate 1, lightly overcast with Spectrum Red, Plate 1.

Petals:

*Texture.*—Leathery; is not affected by wet or hot weather.

*Appearance.*—Inside—velvety. Outside—satiny.

*Form.*—Oval.

*Arrangement.* — Imbricated (regularly arranged single-like).

*Petaloids in center.*—Few; small.

*Persistence.*—Drop off cleanly.

*Fragrance.*—Moderate. Nature—tea (average hybrid tea scent).

*Lasting quality.*—On the plant—long. As cut flower—long.

*Genital organs*

Stamens, anthers: Medium size; many; regularly arranged around styles. Color—Ochraceous-Orange, Plate 15.

Stamens, filaments (threads): Medium length. Color—Indian Lake, Plate 26.

Pollen: Color—Pale Ochraceous-Buff, Plate 15.

Styles: Loosely separated; uneven length; medium length; thin.

Stigmas: Color—Warm Buff, Plate 15.

Ovaries: Some protruding from calyx.

Hips: None.

Seeds: None.

*Plant*

Form: Bush.

Growth: Vigorous; upright.

Foliage: Compound of 3–5 leaflets.

*Size.*—Medium.

*Quantity.*—Abundant.

*Color.*—New foliage: upper side—Oil Green, Plate 5, with edge of leaf lightly overcast with Acajou Red, Plate 13; under side—Biscay Green, Plate 17, with edge of leaf lightly overcast with Acajou Red, Plate 13. Old foliage: upper side—Cress Green, Plate 31; under side—light Cress Green, Plate 31.

*Shape.*—Oval.

*Texture.*—Upper side—leathery. Under side—smooth.

*Ribs and veins.*—Ordinary.

*Edge.*—Serrated (saw-toothed).

*Serrations.*—Both double and single; small.

*Leaf stem.*—Color—Jade Green, Plate 31. Under side—prickly.

*Stipules.*—Medium length; smooth.

Wood:

*New wood.*—Color—Oil Green, Plate 5. Bark—smooth.

*Old wood.*—Color—Cress Green, Plate 31. Bark—smooth.

Thorns:

*Thorns.*—Quantity: on main stalks from base—ordinary; on laterals from stalk—ordinary. Form—narrow base; medium length; straight. Color (when young)—Hydrangea Red, Plate 27. Position—irregular.

*Prickles.*—Quantity: on main stalks—none; on laterals—nine.

*Short needles.*—Quantity: on main stalks—none; on laterals—none.

I claim:

A new and distinct variety of rose plant of the hybrid tea class, substantially as herein shown and described, characterized particularly as to novelty by the unique combination of abundant foliage, taller growth than the variety "New Yorker" (Plant Patent No. 823), large flower size, and a very deep red general color tonality of flowers corresponding to Carmine.

No references cited.